United States Patent [19]

Heuscher

[11] Patent Number: 5,396,418
[45] Date of Patent: Mar. 7, 1995

[54] FOUR DIMENSIONAL SPIRAL VOLUME IMAGING USING FAST RETRACE

[75] Inventor: Dominic J. Heuscher, Aurora, Ohio

[73] Assignee: Picker International, Inc., Highland Hts., Ohio

[21] Appl. No.: 139,318

[22] Filed: Oct. 19, 1993

Related U.S. Application Data

[63] Continuation-in-part of Ser. No. 943,411, Sep. 9, 1992, abandoned, which is a continuation-in-part of Ser. No. 567,300, Aug. 14, 1990, Pat. No. 5,262,946, which is a continuation-in-part of Ser. No. 260,403, Oct. 20, 1988, Pat. No. 4,965,726, and a continuation-in-part of Ser. No. 438,687, Nov. 17, 1989, Pat. No. 5,276,614.

[51] Int. Cl.⁶ .............................................. G06F 15/42
[52] U.S. Cl. ............................................... 364/413.18
[58] Field of Search .................. 364/413.18, 413.15, 364/413.19; 378/12, 14, 15, 17

[56] References Cited

U.S. PATENT DOCUMENTS

| | | | |
|---|---|---|---|
| 4,442,489 | 4/1984 | Wagner | 364/414 |
| 4,672,651 | 6/1987 | Horiba et al. | 378/62 |
| 4,789,929 | 12/1988 | Nishimura et al. | 364/413.15 |
| 5,073,911 | 12/1991 | Ozaki et al. | 378/17 |
| 5,287,274 | 2/1994 | Saint Felix et al. | 364/413.15 |

FOREIGN PATENT DOCUMENTS

| | | |
|---|---|---|
| 383232A3 | 8/1990 | European Pat. Off. |
| 426464A3 | 5/1991 | European Pat. Off. |

OTHER PUBLICATIONS

Power–injected CT Contrast Opacifies Vascular Spaces, S. D. Lane, Diagnostic Imaging, Nov. 1988.
Spiral Volumetric CT with Single Breath–Hold Technique, Continuous Transport, & Continuous Scanner Rotation, Kalender, et al., Radiology, 1990; 176:181–183.
Physical Performance Characteristics of Spiral CT Scanning, Kalender, et al. Med. Phys. 18 (5) Sep./Oct. 1991, pp. 910–915.
World's Fastest CT From Zero to 40 in 75 Seconds, Picker Advertisement.

*Primary Examiner*—Donald E. McElheny, Jr.
*Attorney, Agent, or Firm*—Fay, Sharpe, Beall, Fagan, Minnich & McKee

[57] ABSTRACT

A subject in an examination region (14) moves axially as an x-ray source (12) rotates therearound. Views corresponding to a spiral path around a volume of interest in the patient are sampled, interpolated (46), and reconstructed (54) into a three-dimensional image representation (56). This process is repeated a plurality of times to generate a plurality of three-dimensional image representations of the same volume at time displaced intervals. The plurality of image representations are temporally interpolated (110) to generate a series of image representations, each one of which represents the same time or time interval, i.e., a four-dimensional image representation that is linear in all four dimensions. Preferably, a contrast agent is injected into the patient such that the data represents the movement of contrast agent through the volume of interest. A reference image representation (126) of the volume of interest with no contrast agent is subtracted (124) from the four-dimensional image representation to generate a four-dimensional image (128) of the movement of the contrast agent through the volume of interest.

24 Claims, 16 Drawing Sheets

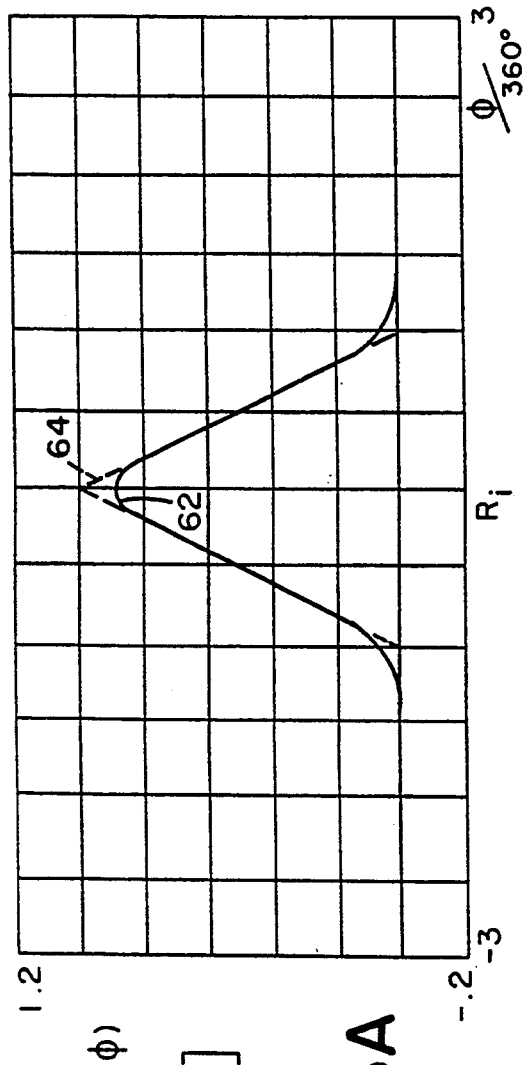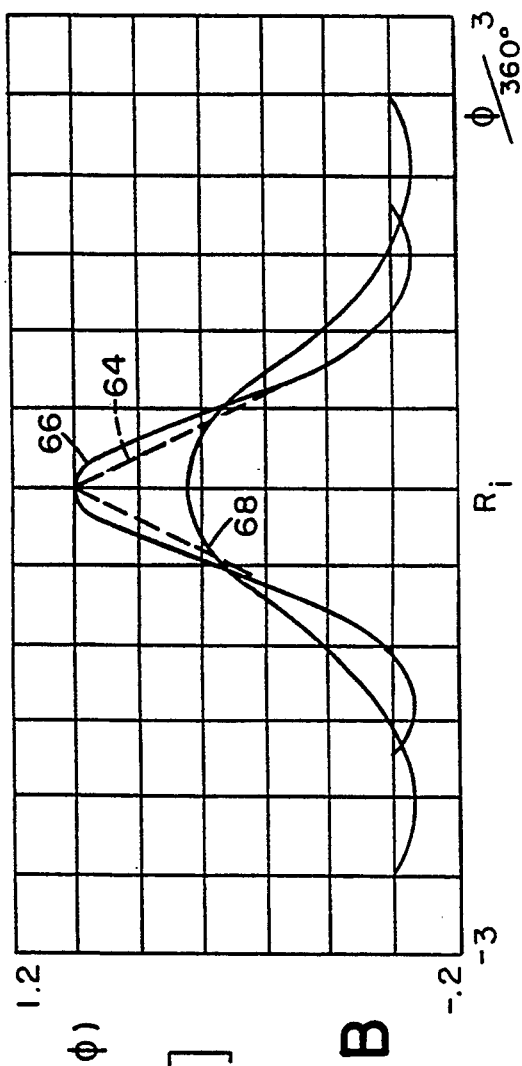

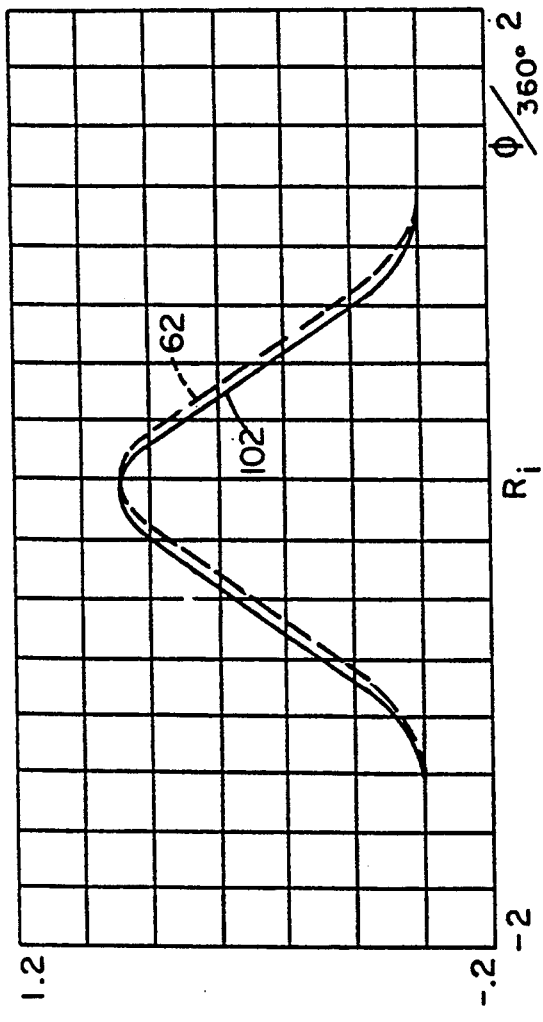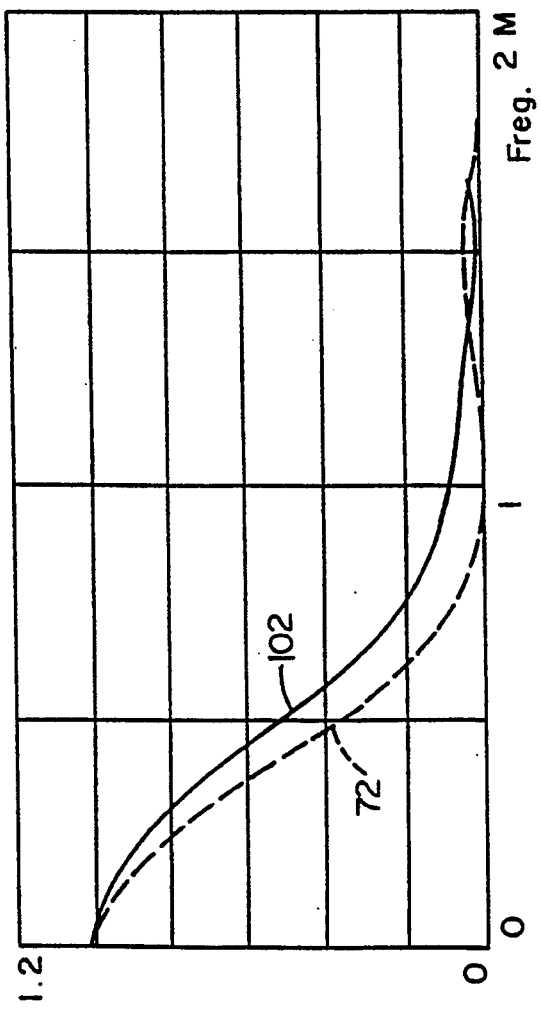

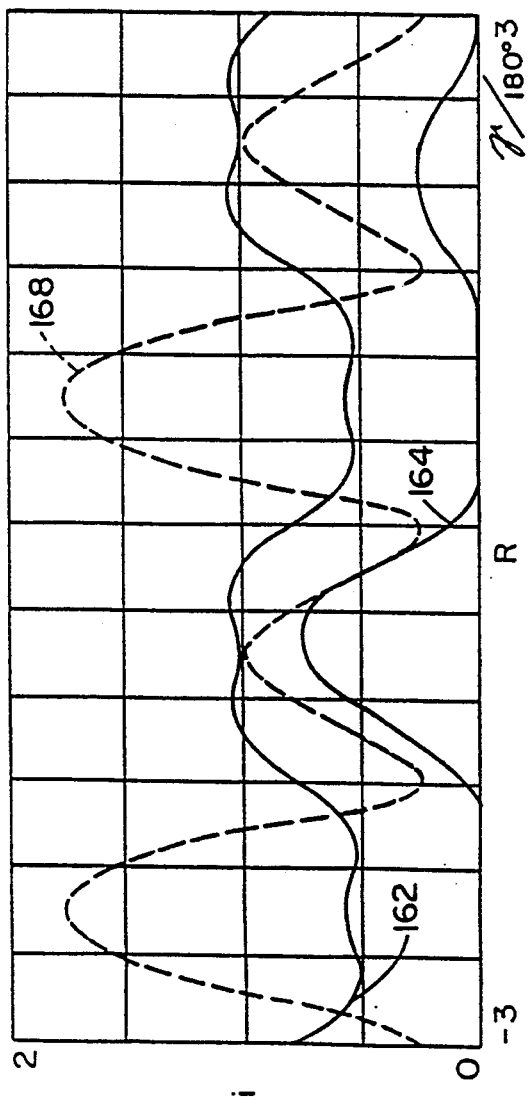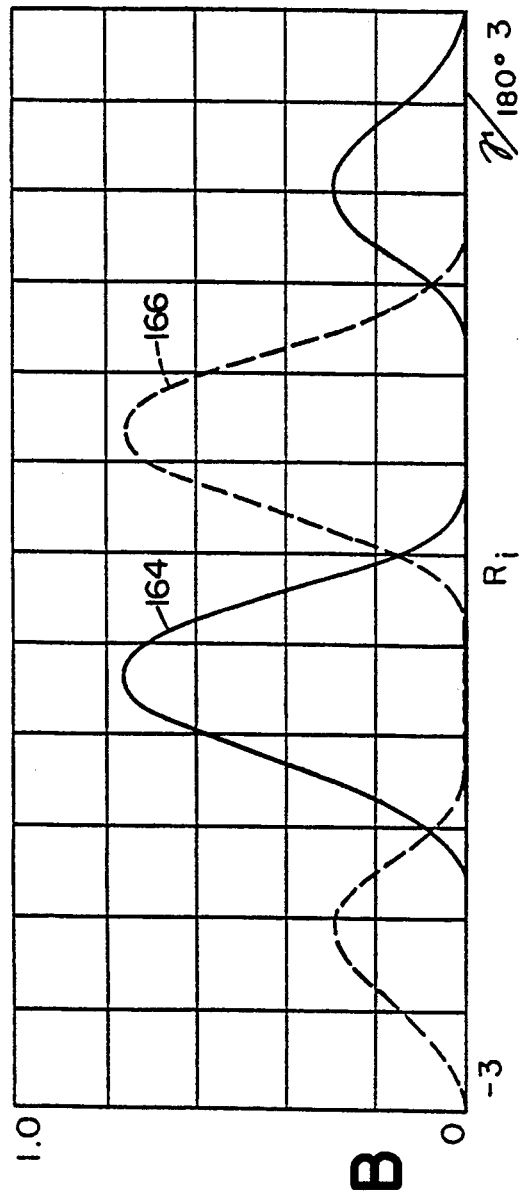

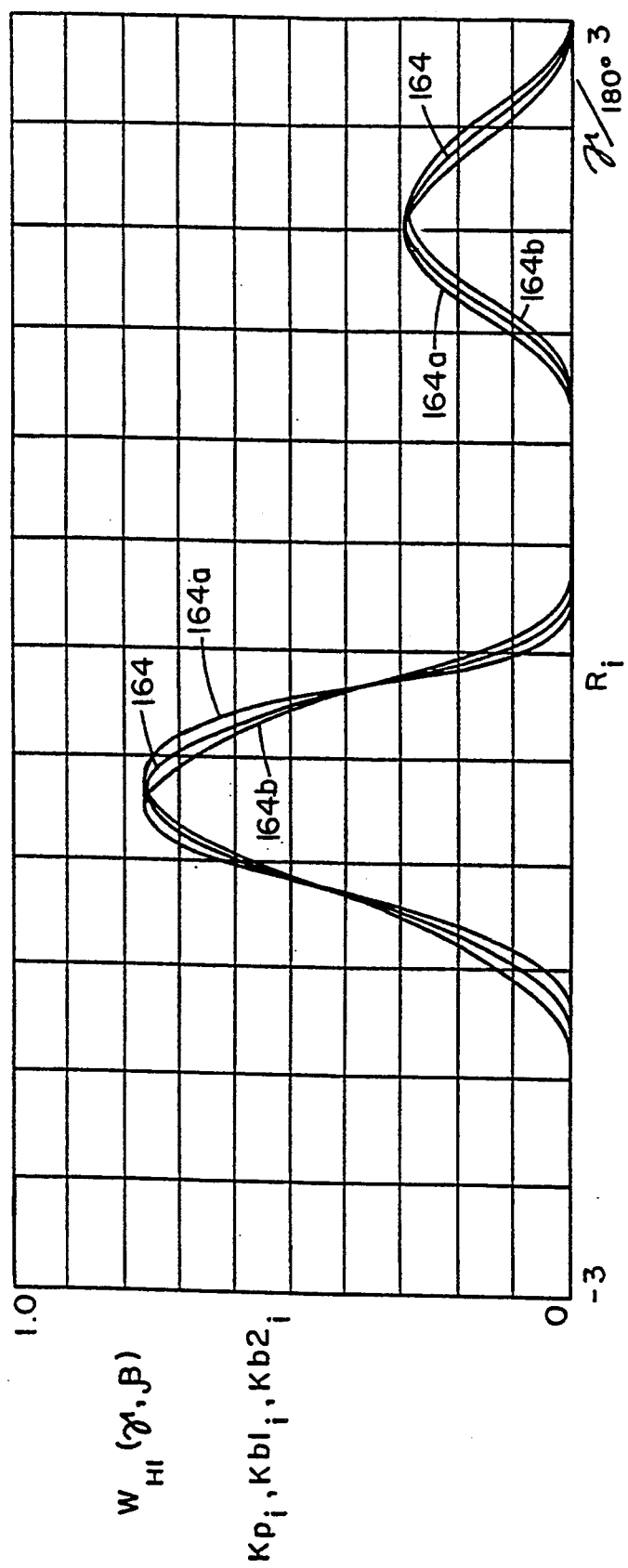
FIG. IIC

FOUR DIMENSIONAL SPIRAL VOLUME IMAGING USING FAST RETRACE

This application is a continuation-in-part of U.S. application Ser. No. 07/943,411, filed Sep. 9, 1992, now abandoned, which application in turn, is a continuation-in-part of U.S. application Ser. No. 07/567,300, U.S. Pat. No. 5,262,946, filed Aug. 14, 1990, which is a continuation-in-part of U.S. application Ser. No. 07/260,403, filed Oct. 20, 1988, now U.S. Pat. No. 4,965,726 and U.S. application Ser. No. 07/438,687, U.S. Pat. No. 5,276,614, filed Nov. 17, 1989.

BACKGROUND OF THE INVENTION

The present invention relates to the art of medical diagnostic imaging. It finds particular application in conjunction with spiral volume imaging with CT scanners and will be described with particular reference thereto. However, it is to be appreciated that the invention will also find application in conjunction with other types of volume imaging, with multiple single slice images, continuous rotating x-ray source images, gated imaging, and the like.

In spiral or helical scanning, the x-ray source or tube rotates continuously as the patient support table moves at a constant, linear velocity. In this manner, the collected data effectively represents a helical path of constant pitch through the patient. Conventionally, the data is stored and handled as a series of parallel planes, transverse to the longitudinal axis of the patient, or more specifically, as a three dimensional rectangular matrix of memory cells. See, for example, U.S. Pat. No. 3,432,657 to Slavin.

For some medical diagnoses, it is advantages to inject a patient with a contrast agent, usually a high-Z contrast material such as iodine. Depending on how far the imaged region is from the heart, the contrast material maintains its peak concentration level in the region of interest over a period of about 30–90 seconds. CT scanning techniques have been developed for generating images of the region of interest while the contrast agent is near its peak. For example, ultra fast CT, i.e. electron beam scanning, has been used to cover a significant volume. See "Power-Injected CT Contrast Opacifies Vascular Spaces", Sam D. Lane, Diagnostic Imaging, November 1988. However, this technique cannot show contrast variations over a significant volume over a period of time. Lane must leave the couch in one position in order to show contrast variations of the same region over time. Thus, the Lane technique is disadvantageous due to the increased dose of contrast agent and the limiting of measurements to only a single observed axial slice.

A volume helical scanning technique is discussed in U.S. Pat. No. 4,789,929 of Nishimura, et al. which utilizes back and forth motion of the couch to achieve more complete sampling of the volume being scanned. Nishimura does not address the concept in a temporal dimension. Moreover, the back and forth movement during data collection results in a temporally non-uniform sampling, particularly for regions of interest near the ends of the volume.

Spiral volume scans have been performed over a single patient breath-hold in the presence of a contrast agent. See "Spiral Volumetric CT with Single-Breath-Hold Technique, Continuous Transport, and Continuous Scanner Rotation", Radiology, Vol 176, pp 181–183, 1990 and "Physical Performance Characteristics of Spiral CT Scanning", Med. Phys. Vol. 18, No. 5, September/October 1991, both by Kalender, et al. One drawback of these techniques is that they use a linear interpolator for the helical interpolation, which reduces sharpness of the CT slice definition. Another drawback is that only one set of measurements is obtained from a single breath-hold.

In order to fit the spiral collected data into a conventional three dimensional rectangular matrix, a series of parallel planes are defined through the spiral collected data, with a one plane per spiral revolution, e.g. at each 0° of source rotation. During the data collection period, a series of views or fans of data are collected at preselected angular increments around the patient. Potentially, one view per plane, by convention the 0° or 12 o'clock view, falls squarely in the plane requiring no averaging or weighting. For each remaining view of the plane, there is a pair of corresponding views or data fans, one from the revolution preceding the plane and the other from the revolution following the plane. These views are averaged or weighted in accordance with their relative distance from the plane. In this manner, a full set of weighted views is created to perform a conventional 360° CT reconstruction algorithm. See U.S. Pat. No. 4,630,202 issued December 1986 to Mori.

One of the problems with the linear interpolation technique is that it introduces errors in fourth generation scanners using source fan reconstruction. In a third generation scanner in which the x-ray source and an arc of detectors rotate together about the slice, each data fan or view is collected instantaneously in a plane parallel to the artificially defined transverse slices. In a fourth generation scanner, there is a parallel ring of stationary detectors surrounding the patient. With source fan reconstruction, each detector is sampled at monitored, time displaced intervals generating a view or fan of data as the source rotates behind the examination region. Because the patient moves longitudinally between the first and last data sampling of the view or data fan, the views are warped or canted along the spiral path. The linear interpolation scheme which assumes that the views lie parallel to the artificially defined planes introduces errors.

Another problem with the linear interpolation technique is that it is particularly sensitive to variations in the x-ray rotation speed, the velocity with which the patient is moved, and fluctuations in the output of the x-ray tube.

The present invention provides a new and improved spiral volume imaging technique.

SUMMARY OF THE INVENTION

In accordance with the present invention, a plurality of helical volume scans are repeatedly conducted over a duration in which a contrast agent is present in a volumetric region of interest.

More specifically, axial movement is timed such that a plurality of helical scans are generated while the contrast agent is present in the region of interest. Between helical scans, the patient and CT scanner are repositioned at the beginning of the helix at a more rapid rate than during the helical scanning. In this manner, each helical scan is conducted in the same direction for temporal consistency.

In accordance with another aspect of the present invention, the volumetric image data is organized by spatial position and time of data acquisition. The data is temporally interpolated to generate a plurality of temporal data sets which each represent the volume substantially at a single period of time.

More specifically to the preferred embodiment, the data is spatially interpolated into a rectangular three-dimensional grid of data values and temporally interpolated to generate a plurality of the three-dimensional grids at uniform, time displaced intervals.

In accordance with another aspect of the present invention, data sets from each of a plurality of volumetric scans are aligned before performing the temporal interpolation.

In accordance with a more limited aspect of the present invention, one or more characteristic points in each temporally displaced volume are identified and the spatial coordinates are shifted such that the characteristic points in each volume coincide.

One advantage of the present invention is that it enables contrast measurements of a volume to be taken over time.

Another advantage of the present invention is that it maintains a high volume of interest resolution both spatially, due to a high resolution interpolation and temporally, due to a rapid retrace and same direction spiral scanning.

Another advantage of the present invention is that flow and perfusion measurements can be made.

Another advantage of the present invention is that multiple-breath-hold measurements can be made.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIGS. 3A-3D are illustrative of different weighting functions for weighting among the more than two helical rotations;

FIGS. 7A-7D are illustrative of compensations for gantry rotation and table speed variations, particularly variations in weighting functions for effecting the correction;

FIGS. 11A-11C are illustrative of x-ray current and kV fluctuations and corresponding weighting functions for dual kV imaging.

DETAILED DESCRIPTION OF THE PREFERRED EMBODIMENTS

Figure 1A:
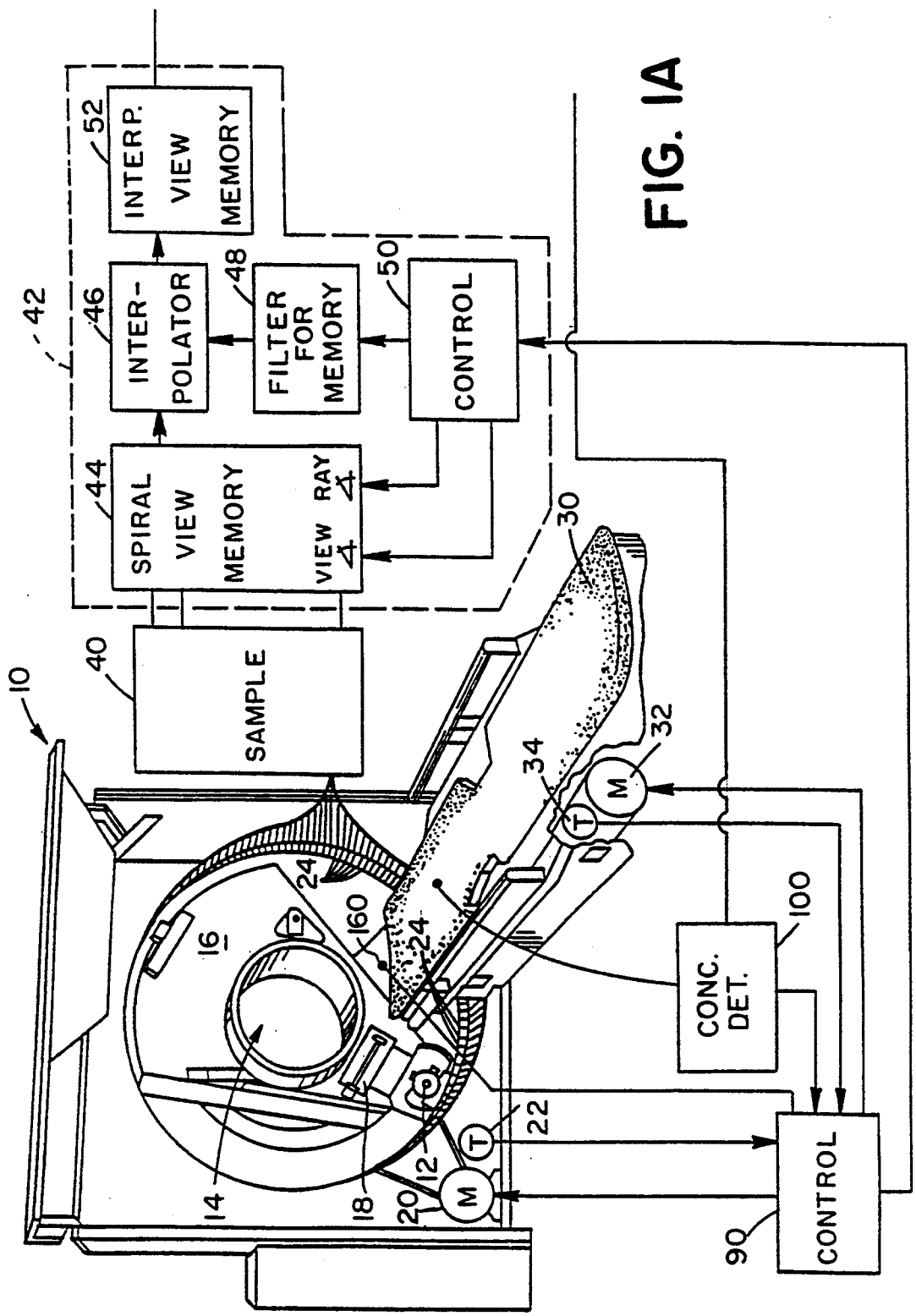
FIG. 1A and 1B taken together are a diagrammatic illustration of a CT scanner in accordance with the present invention.

With reference to FIG. 1A, a CT scanner 10 includes a radiation source 12, such as an x-ray tube, for projecting a fan beam of radiation through an examination region or scan circle 14. The x-ray tube is mounted on a rotatable gantry 16 to rotate the fan beam of radiation around the examination region. A collimator and shutter means 18 collimates the beam of radiation to one or more narrow planar beams and selectively gates the beam on and off. The beam may be also gated on and off electronically at the x-ray tube. A motor 20 provides motive power for rotating the gantry 16 continuously around the examination region. A rotational position encoder 22 is connected with the motor and the gantry to measure the rotational position of the gantry. In the illustrated fourth generation CT scanner, a ring of radiation detectors 24 are mounted peripherally around the examination region. For mechanical and mathematical convenience, the detectors 24 are stationarily mounted around the rotating gantry in the same plane as the x-ray tube.

Figure 2:
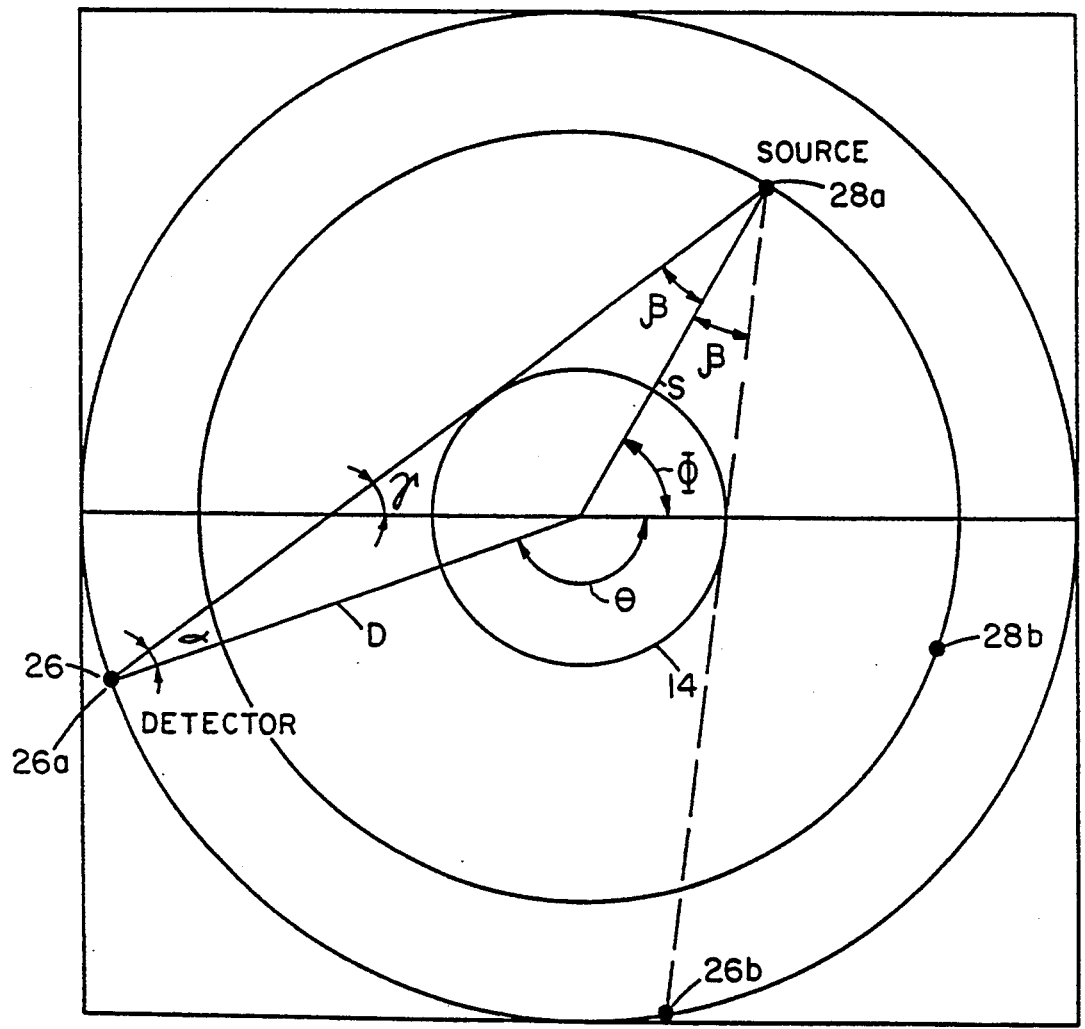
FIG. 2 illustrates the geometry of a CT scanner.

With reference to FIG. 2, an arc of the detectors are sampled concurrently at short time increments as the radiation source 12 rotates in back of the examination region 14 to generate views or fan data sets. To generate detector fans which span an angle $2\alpha$, an exemplary detector 26 at an angular position $\theta$ is first sampled when the radiation source is at a location $28a$ tangent to one side of the examination region 14 and monitored incrementally until the radiation source reaches a point $28b$ in a line from the detector tangential to the other side of the examination region. For a source fan geometry, each of the detectors between detectors $26a$ and $26b$ are sampled concurrently to generate a source fan view or data set. The collected source fan data set can be identified by the angular position $\Phi$ of its apex around the examination region. Each ray of data between the source and one of the detectors is described by an angle $\beta$. Each ray of the source fan also is identifiable by its angle $\gamma$ relative to the common axis. The source is disposed a radius S from the center of the examination region and the ring of detectors 24 is disposed a radius D from the center of the examination region. In a third generation scanner in which the invention is equally applicable, a single arc of detectors between detectors $28a$ and $28b$ are mounted to the gantry 16 for rotation with the source. A third generation source fan geometry is described mathematically the same.

With reference again to FIG. 1A, a patient couch 30 supports a subject, particularly a human patient, in a reclined position. A means, such as a motor 32, advances the patient supporting surface of the couch through the examination region at a selectable velocity. An encoder 34 is connected with the motor 32, the moveable patient supporting portion 30, and the drive mechanism therebetween for monitoring the actual position of the patient supporting surface as it moves the patient through the scan circle 14.

A sampling means 40 samples the views or data sets corresponding to each angular position around the examination region 14 for each of a multiplicity of helical scans. A view processor 42 converts the spiral sampled views of each helical scan into a plurality of image representations corresponding to parallel planes sampled over a limited time range. The view processor includes a view memory 44 in which the view data stored and addressable by a combination of the scan number, (or time), rotation number, view angle, and ray angle within the view. The view processor 42 further includes a filter or interpolation means 46 for interpolating the data of each helical scan in the spiral view memory 44 into parallel slice data. The interpolation means 46 operates on a plurality of views of corresponding view angle with a filter or interpolation function supplied by a filter function memory 48.

Figure 1B:
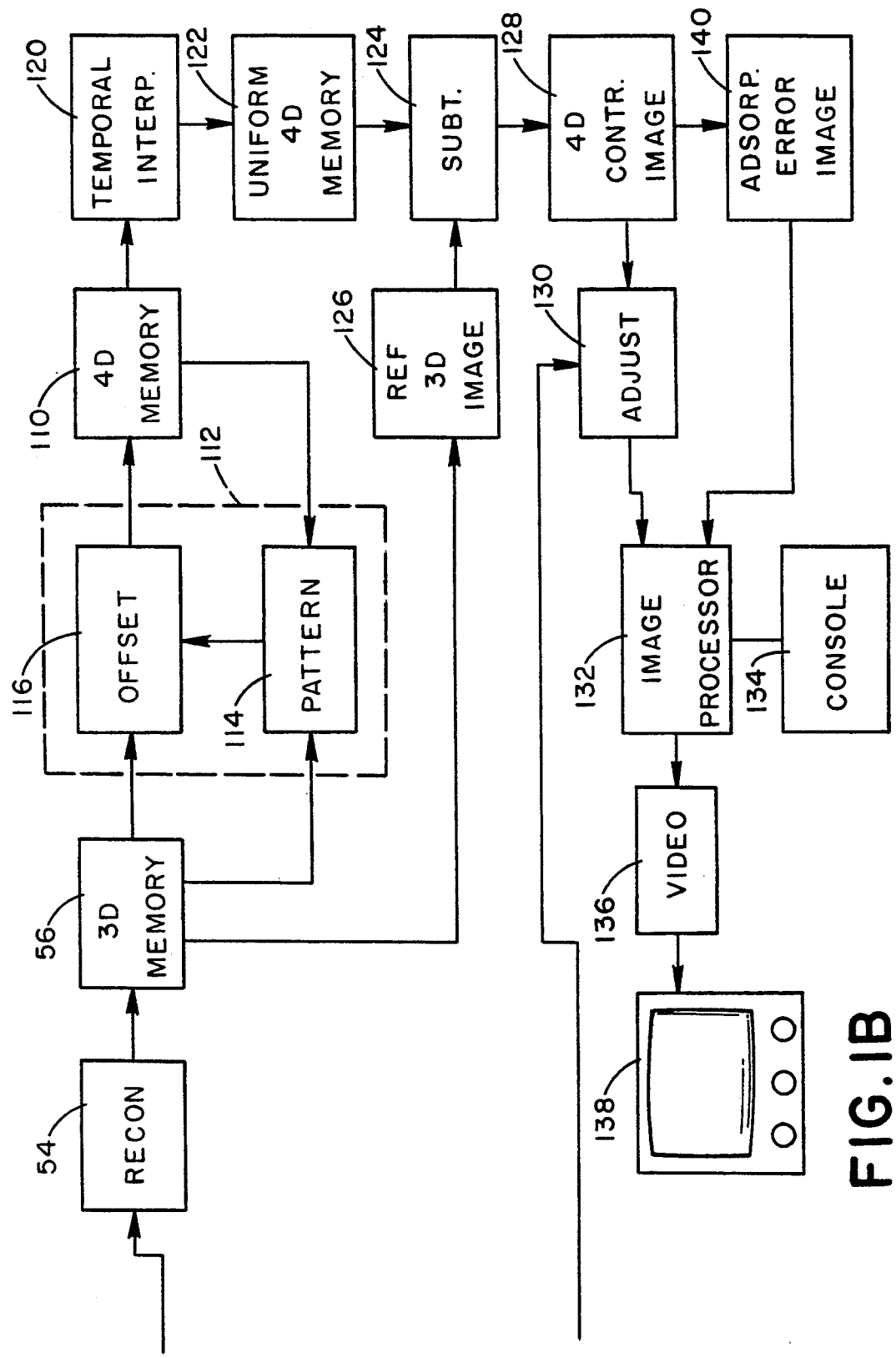

With continuing reference to FIG. 1A and further reference to FIG. 1B, a control means 50 indexes the view angle to each of the view angles in a complete helical scan, e.g. the views disposed at regular increments 360° around the examination region. A plurality of views corresponding to each individual view angle are transferred to the interpolation means to be filtered into an interpolated view. Each interpolated view is stored in an interpolated view memory means 52 until the interpolated views corresponding to each interpolated slice of one helical scan are generated. Thereafter, an image reconstruction means 54 uses a conventional filtered backprojection or other reconstruction algorithm to reconstruct each of a plurality of slices and store the resultant slices from each helical scan in a three-dimensional volume data memory 56. For each helical scan, the volume data memory means stores a rectangular pixel array corresponding to each of a plurality of slices, the slices being spaced a distance commensurate with the resolution of the pixels in each slice. In this manner, each set of data stored in the volume data memory means can be conceptualized as a rectangular data volume corresponding to one of the helical scans.

With reference to FIG. 3A, the filter function memory means 48 stores a plurality of filter or interpolation functions. FIG. 3A compares a modified linear weighting function 62 with a prior art linear weighting 64. The modified linear weighting function $W(\phi)=0$ for $|R|>1.5$ with an average width of 1.1, where $\phi=R.360°$. $W(\phi)$ and its first derivative are both continuous as is represented by the rounding adjacent $R=0$ and $R=\pm 1$. The rotational index R is the sum of the integral rotation index m and the fractional rotation r. Moreover, the weighting function has unity weighting, i.e.

$$\sum_m W(\phi_m) = 1, \text{ for } 0 < r < 1, \quad (1)$$

where $$\Phi_m = (r+m)360°$$

and the first moments are equal to zero, i.e.

$$\sum_m (r + m) \cdot W(\phi_m) = 0, \text{ for } 0 < r < 1. \quad (2)$$

In FIG. 3B, a cubic weighting function 66 which spans four contiguous rotations is compared with the conventional linear interpolation 64. In the cubic interpolation, $$W(\phi)=0, \text{ for } |R|>2 \quad (3)$$

with an average width $\approx 1.1$. $W(\phi)$ and its first derivative are again continuous and the conditions of Equations (1) and (2) are also valid. Analogously, a cubic weighting of the form 68 may also be utilized where:

$$W(\phi)=0, \text{ for } |R|>3 \quad (4)$$

and with a width (at half height) equal to 1.6 rotations.

Figure 3C:
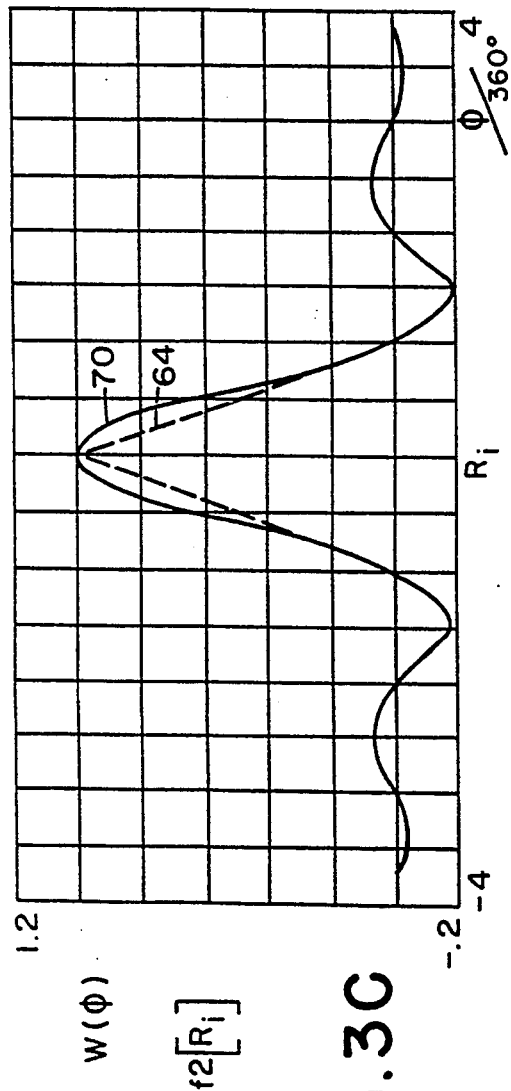

FIG. 3C compares the conventional linear weighting 64 with a 7-lobe helical weighting function 70 where:

$$W(\phi)=0, \text{ for } |R|>4 \quad (5)$$

Again, the function and its first derivative are continuous and the conditions of Equations (1) and (2) are met.

Figure 3D:
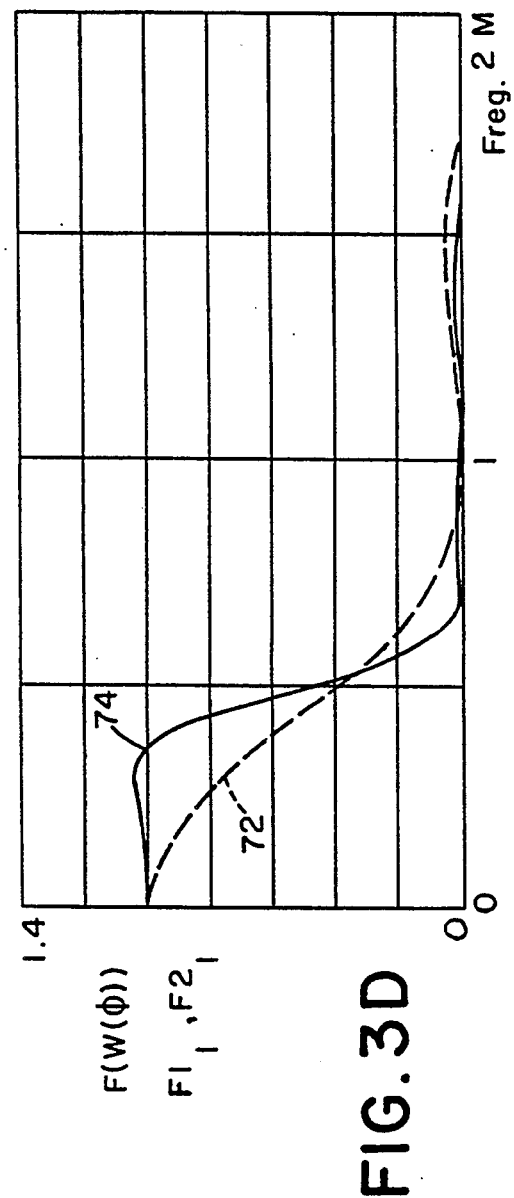

With reference to FIG. 3D, the conventional linear weighting of curve 64 has a relatively limited frequency response 72 along the z-axis. By distinction, the 7-lobed helical weighting function 70 has a much crisper frequency response 74 in the z direction. Note that the frequency response of the 7-lobed helical weighting 74 is relatively flat and drops off relatively quickly which eliminates the smoothing heretofore required with the linear weighting function.

It should be noted that the revolution number or longitudinal position R in FIGS. 3A-3D is not measured digitally. That is, if the detector crosses the even integer values $R=0$, $\pm 1$, $\pm 2$, etc, at 0°, then at 90°, the R position is $-0.75$, $+0.25$, $+1.25$, etc.

In accordance with another embodiment of the present invention, the reconstruction means 54 uses a reconstruction algorithm based on views spanning 180° plus the fan angle, such as the algorithm illustrated in U.S. Pat. No. 4,293,912 issued October 1981 to Walters. To utilize the 180° redundancy in the data most effectively with interpolation functions of the shapes described above but of half the extent, the interpolating filter from filter memory 48 is redefined on a 180° basis. Specifically, the linear weighting 64 would result in a warped rather than a planar image representation.

Figure 4A:
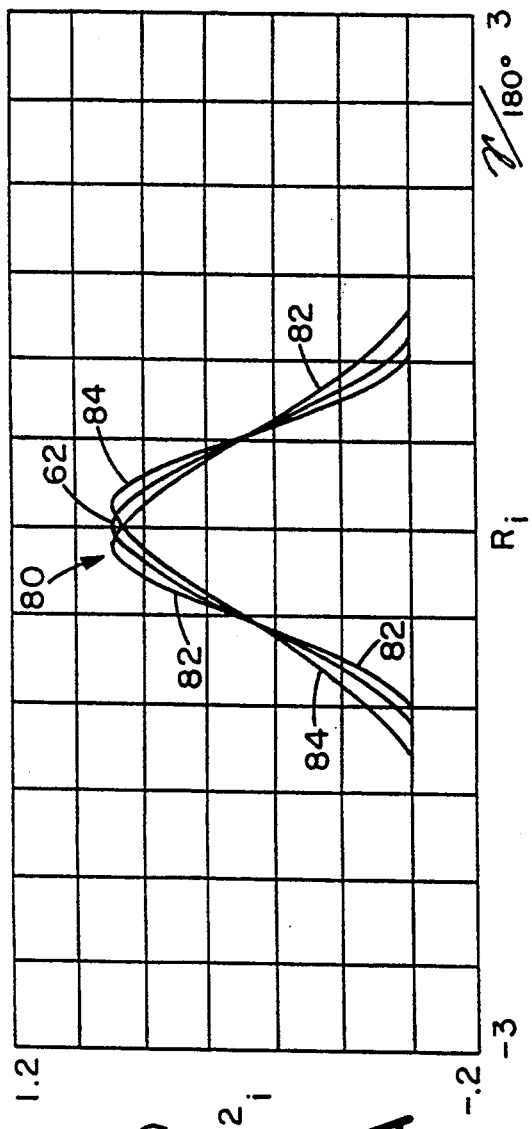
FIGS. 4A and 4B are illustrative of interpolation or weighting functions for 180° based reconstruction algorithms.

With reference to FIG. 4A, a preferred technique for using 180° basis reconstruction techniques is to use a weighting function based on both the view angle and the angle of each individual ray within the view. Curve set 80 includes the modified linear function 62 for the center or zero ray of the view or fan. Curve 82 illustrates the modified weighting function shifted for the ray at one extreme of the fan and curve 84 illustrates the modified weighting function shifted for the ray at the opposite extreme of the fan. For each ray in between, the extreme and central rays, the weighting function is shifted a fraction of the illustrated difference. Each weighting curve and its first derivative are still continuous but now meet the conditions of Equations (6) and (7) below. The sum of the weighting functions for rays which are 180° opposite to each other is equal to one.

$$\sum_m W(\gamma_m, (-1)^m \beta)) = 1, \text{ for } \gamma_m = (r + m) \, 180° \quad (6)$$

Also, the first moments are equal to zero, i.e.

$$\sum_m \left( r + m + \frac{(-1)^m \beta}{180} \right) \cdot W(\gamma_m, (-1)^m \beta) = 0. \tag{7}$$

For projection data organized in the form of source fans $V_s(\Phi + n.360°, \beta)$, the longitudinal interpolation generates:

$$D_{180}(\phi, \beta) = \sum_n W_s(\phi + n \cdot 360°, \beta) \cdot V_s(\phi + n \cdot 360°, \beta) \tag{8a}$$

where:

$$W_s(\Phi + n.360°, \beta) = W(\gamma + \beta, \beta)$$

and $W_s(\gamma, \beta)$ is the weighting function that satisfies conditions (6) and (7) and $\phi = 0$ to $360°$ $$\beta = \frac{-\beta_0}{2} \text{ to } \frac{\beta_0}{2}$$

$\beta_0$ = fan angle defining the scan circle.

The resulting 360° of projection data $D_{180}(\phi, \beta)$ no longer has unity weighting, but instead has an average weighting spanning 180°. This data can be reconstructed using standard convolution backprojection of $D_{180}(\phi, \beta)$ for $\phi = 0$ to $360°$. For projection data organized as detector fans $V_D(\theta + n.360°, \alpha)$, the longitudinal interpolation generates:

$$D_{180}(\theta, \alpha) = \sum_n W_D(\theta + n \cdot 360°, \alpha) \cdot V_D(\theta + n \cdot 360°, \alpha) \tag{8b}$$

where $W_D(\theta + n.360°, \alpha)$ is obtained by remapping $W_s(\phi + n.360°, \beta)$ from source fan format to detector fan format. Again, this data can be reconstructed using standard convolution backprojection of $D_{180}(\theta, \alpha)$ for $\theta = 0°$ to $360°$.

Figure 4B:
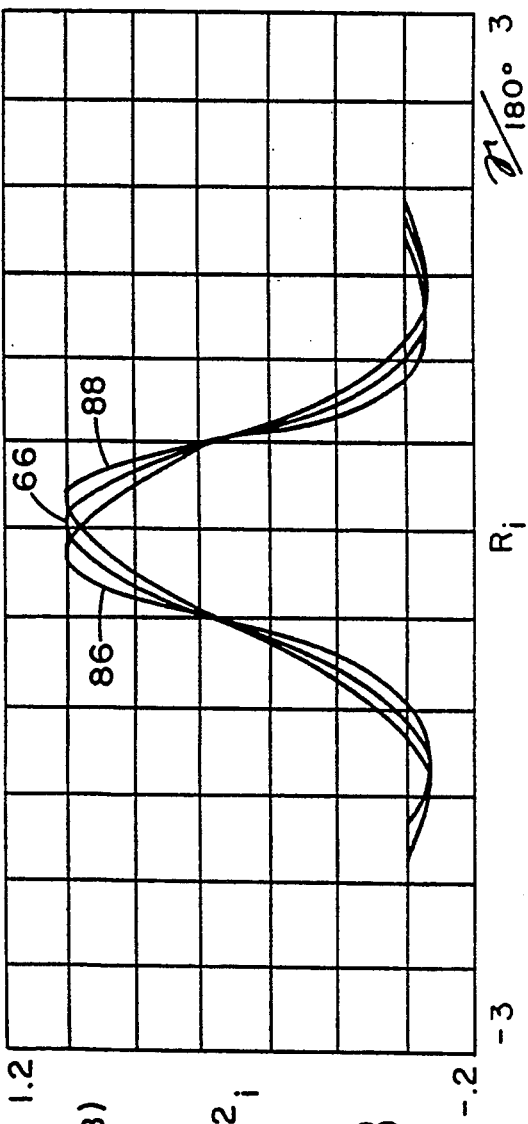

Analogously, the weighting function $W_{180}(\gamma, \beta)$ for the cubic weighting function of curve 66 of FIG. 3B can be made ray dependent as illustrated in FIG. 4B. Specifically, cubic weighting function 66 is used for the central ray. For the ray at one extreme, the weighting function is distorted as illustrated by curve 86 and for the ray of the other extreme of the fan, the weighting curve is distorted as illustrated at 88. In the illustrated embodiment, the extreme rays of curves 86 and 88 are for $\beta = \pm 23°$.

Figure 5A:
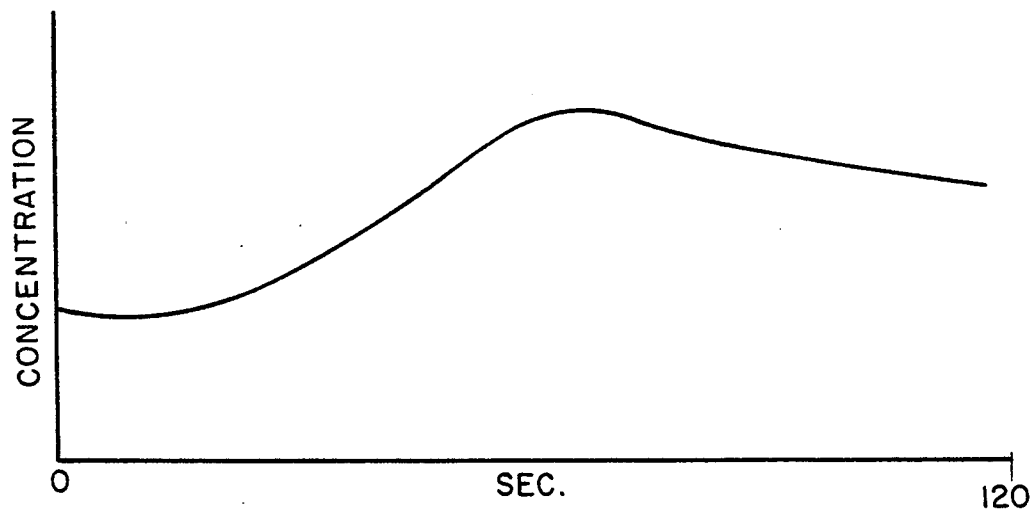
FIGS. 5A and 5B illustrate contrast agent concentration versus time curves for the liver and aorta, respectively.
Figure 5B:
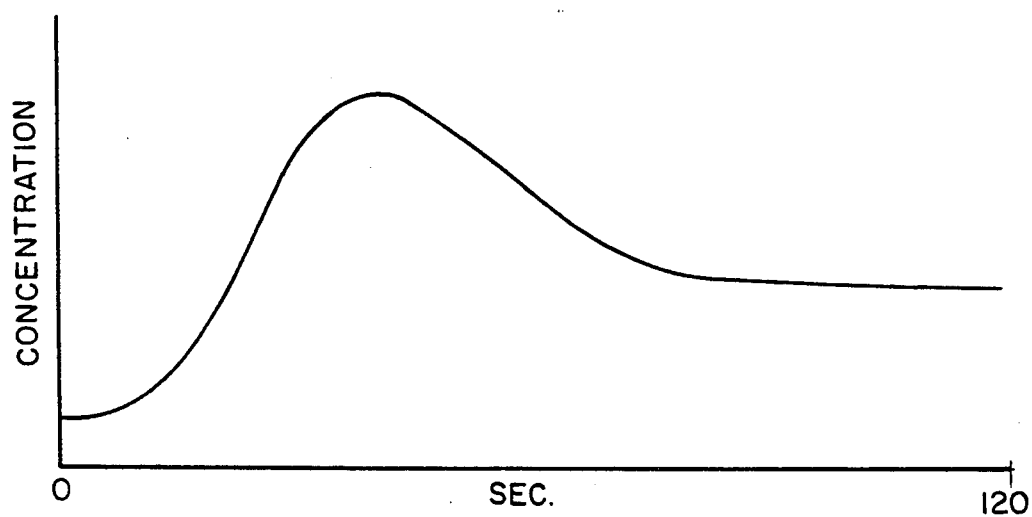

In contrast imaging, a contrast agent is injected into the patient. The concentration of contrast agent at a region of interest varies with time in accordance with a distance of the region of interest from the heart, the rate of injection, and the like. FIG. 5A is typical of contrast agent concentration versus time for the liver and FIG. 5B is typical of contrast agent versus time for the aorta. For four-dimensional images, the above-described imaging process is repeated a plurality of times while the concentration of the contrast agent is near its peak. Additionally, three-dimensional volumetric data sets collected before and after the peak in order to provide a baseline for the contrast agent.

Figure 6:
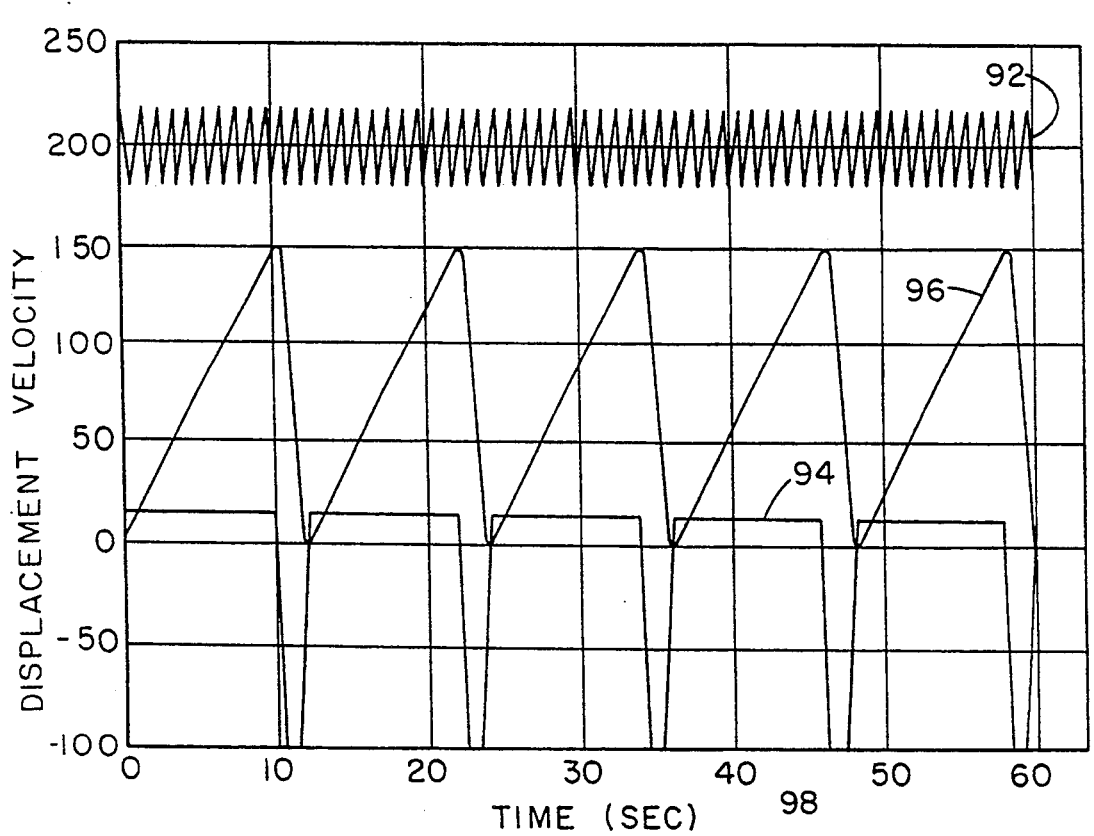
FIG. 6 illustrates helical rotation angle, couch position, and couch velocity for a 15 cm volume covered using a 10 second scan at 1 second/revolution.

With reference again to FIGS. 1A and 1B and further reference to FIG. 6, a control means 90 controls the motors 20 and 32 such that the x-ray source is rotated 92 at about 1 second/revolution and the patient table is moved at about 15 mm/second. This enables a volume which is 15 cm in the axial direction 96 to be covered in 10 seconds. The control 90 then reverses the couch control motor 32 and operates it a higher speed, e.g. 7.5 cm/second, such that the couch is returned 98 to its starting position in about 2 seconds. The control 90 also gates the x-ray tube off or closes the shutter 18 such that the patient is not irradiated during the return or retrace period. This process is then repeated, generating a full set of volume image data about every 12 seconds, i.e. 5 sets/minute.

A concentration agent concentration means 100 signals the control means 90 when the scans are to begin. The contrast agent concentration means 100 may monitor the actual concentration of the contrast agent within the patient. Preferably, because the time from the introduction of the contrast agent until it approaches its peak concentration is well-established medically, the contrast agent concentration means simply times the appropriate duration between introduction of the contrast agent until the known time parameter is reached.

The speed of the table is maintained substantially constant. However, any acceleration at the beginning and deceleration at the end of each helical scan can be readily handled during the interpolation. Moreover, there can be variations in the speed along the scan due to wear, power fluctuations, and the like.

With reference to FIG. 7A, interpolation function 62 is recalculated to function 102 to account for a ±20% sinusoidal speed variation. Specifically:

$$\sum_m W_A(\phi_m) = 1, \text{ for } \phi_m = (r + m) \cdot 360 \tag{9}$$

$$\sum_m P(\phi_m) \cdot W_A(\phi_m) = 0, \tag{10}$$

where $P(\phi)$ is the table position relative to rotational angle $\phi$. Although this satisfies the requirement for planar reconstructions, FIG. 7B shows that the spatial resolution of curve 102 does not match the ideal linear weighting function response 72. However, if the values of the weighting function $W(\phi)$ are remapped to $W(P(\phi))$, a constant spatial response can be maintained. This weighting is adjusted such that:

$$\sum_m W_A(P(\phi_m)) = 1, \text{ for } \phi_m = (r + m) \cdot 360° \tag{11}$$

$$\sum_m P(\phi_m) W_A(P(\phi_m)) = 0. \tag{12}$$

Figure 7C:
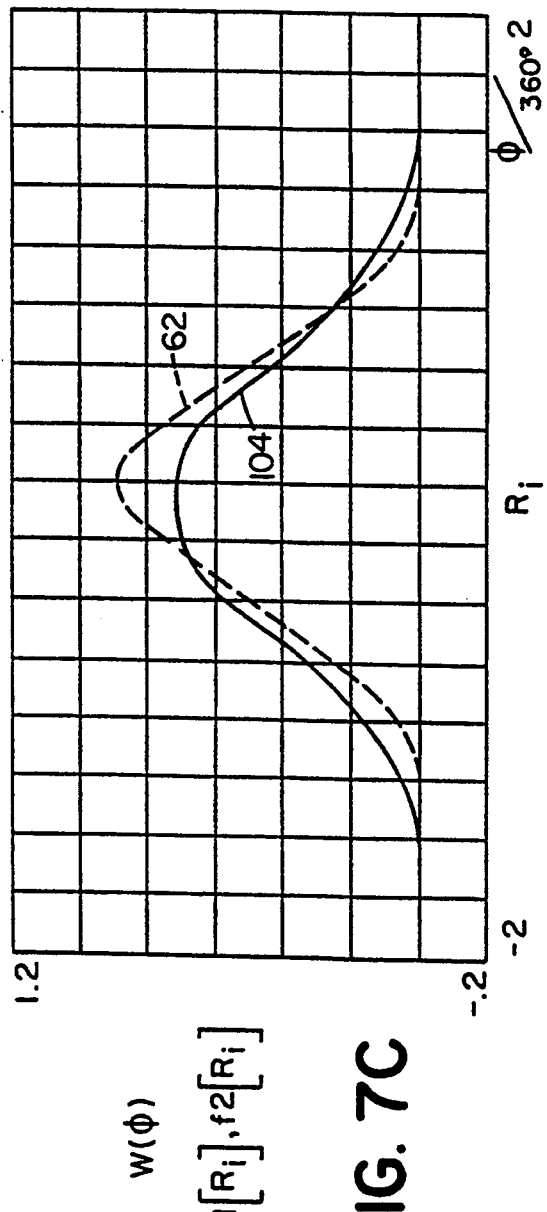
Figure 7D:
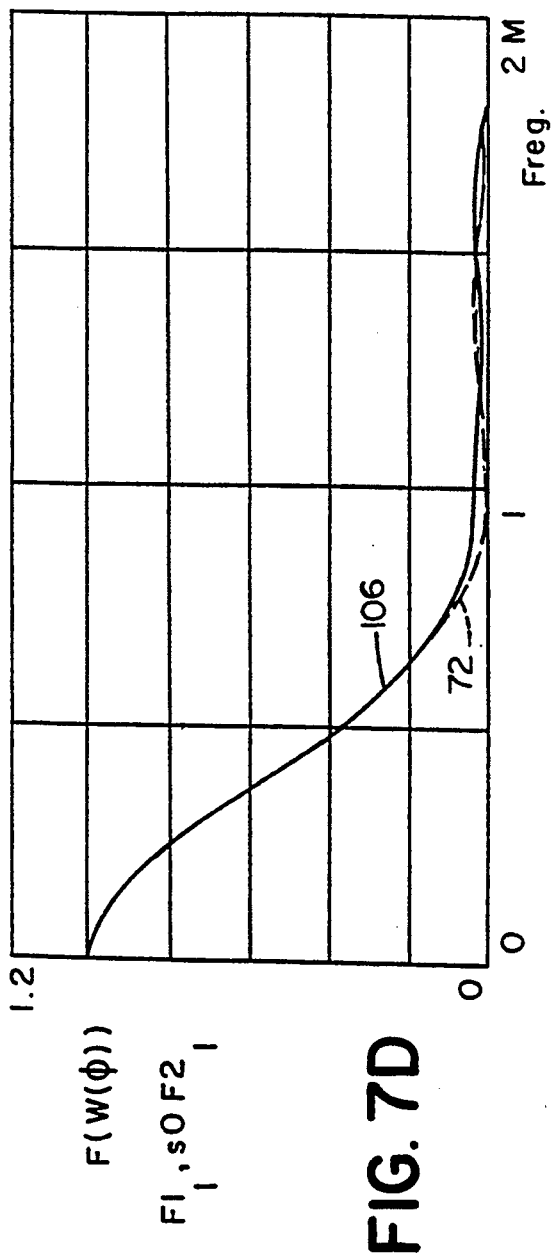

With the new weighting function 104 of FIG. 7C, a spatial response 106 of FIG. 7D is substantially the same as the spatial response 72 of FIG. 7B. In this manner, the interpolation function is utilized to correct for fluctuations in the speeds of relative movement of the source and patient.

As each repetition of the spiral data collection is commenced, the three-dimensional reconstructed image representation is moved from the three-dimensional image memory 56 to a four-dimensional image memory 110, where the fourth dimension is time. An alignment means 112 spatially aligns each three-dimensional volume image with the preceding volume images. A pattern recognition means 114 examines each three-dimensional image representation for one or more characteristic points or structures and compares the spatial location of these characteristic points or structures with the location of the same characteristic point in the four-dimensional memory The characteristic points may be defined by placing x-ray opaque alignment members on the surface of the patient, whose coordinate location in each volume image representation is compared with its location in the preceding volume image representations. An offset means 116 adds an appropriate spatial offset to each image representation in order to bring the characteristic point of the newly acquired volume image representation into alignment with the corresponding characteristic points of previously collected volume image representations. Optionally, the means 116 may also scale the 3D image representation to match the previously acquired data more precisely. Alternately, the recognition means 114 may include a pattern recognition means which examines each image for a characteristic anatomical pattern and compares the position of this characteristic anatomical pattern with the position of the same anatomical pattern in the previously acquired volume image representations in the four-dimensional memory means 110.

As discussed above, each of the spiral data acquisition periods takes some time, 10 seconds in the above example. This causes the data within each three-dimensional image representation to be skewed in time. More specifically, in the above-discussed embodiment, the data at the first end of the volume leads the data at the second end by about 10 seconds. The data at the first end of the next volume trails the data at the second end of the preceding data set by about 2 seconds and the data at the beginning of the last data set by about 12 seconds. A temporal interpolating means 120 interpolates the four-dimensional data in the temporal direction to create data sets which are at even temporal intervals. The temporal and spatially uniform four-dimensional data is stored in a four-dimensional uniform image memory means 122.

For diagnostic purposes, it is often advantageous to generate a display of contrast agent alone. To this end, a subtraction means 124 subtracts a three-dimensional basis or zero contrast agent three-dimensional image from each of the temporally uniform three-dimensional volume images in the uniform volume image memory means 122. More specifically, the control means 90 causes a three-dimensional image taken before the contrast agent is introduced to be loaded into a three-dimensional reference image memory means 126. Optionally, the control means may cause another image to be taken after the contrast agent should have passed out of the region of interest. These before and after three-dimensional image representations can be averaged to form the basis image for storage in the basis volume image memory means 126. Once the substraction means 124 subtracts the basis volume image from each of the temporally displaced volume images, the remainder is a four-dimensional image of the elevation of the contrast agent as a function of time, which contrast agent image is stored in a four-dimensional contrast agent image memory means 128.

As indicated in FIGS. 5A and 5B, the amount of contrast agent within the imaged volume varies with a curve. Where appropriate, an adjustment to the concentration image can be made to account for this temporal variation in concentration agent dose. To this end, a concentration image adjusting means 130 adjusts the four-dimensional contrast image, as may be desired, to account for the temporal variation in contrast image dose. The contrast image concentration curve can be supplied by the contrast agent detection means 100, either by actually measuring the contrast agent or with a priori information. Further, the contrast agent curve can be derived from the contrast agent image 128.

An image and video processor means 132 is controlled by a console 134 to select two-dimensional images from the four-dimensional image data for display. The processor means selects various two-dimensional image representations, such as planar slices through the volume at various angles and at various times, series of images through the same slice showing the evolution over time, projection images, segmented or cut away images, or the like. Moreover the processing means 132 can superimpose data from the reference image from memory 126 with the contrast image 128. For example, it is often advantageous to see the surrounding tissue which is not affected by the contrast agent in order to assist in spatially orienting the radiologist. The background tissue may be displayed in black and white while the contrast image is displayed in other single or multiple color presentations superimposed thereon. A video processor 136 converts the selected two-dimensional image representation(s) into appropriate format for display on a video monitor 138. Optionally, additional image processing means, image memory storage and archiving means, and the like may be provided.

The rate at which the contrast agent reaches each pixel of the image has diagnostic significance. Ideal contrast agent concentration curves for the liver and aorta are shown in FIGS. 5A and 5B. However, because the contrast agent is carried by the blood, failure of the contrast agent to reach a specific pixel in a comparable length of time is indicative of circulatory or other metabolic problems. Optionally, a means 140 examines the corresponding voxel of each of the time displaced three-dimensional images, plots the contrast agent concentration, and compares it to the ideal. From this information, a three-dimensional representation is generated indicating whether each voxel of the volume is receiving the concentration at the proper rate and if not, by how much it is slow. By displaying normal in one color or shade, and regions which receive the contrast agent progressively under the predicted rate in progressively varying colors or shades, valuable diagnostic information can be conveyed. The individual contrast agent versus time curve for each voxel may be displayed individually.

Figure 8:
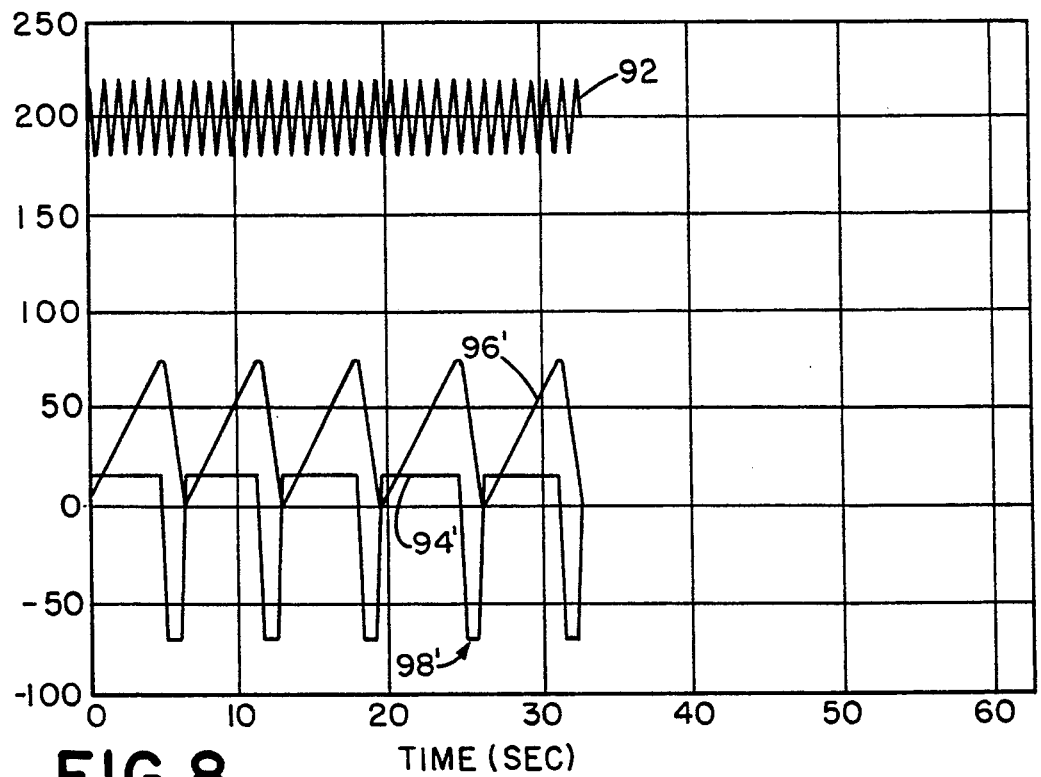
FIG. 8 is analogous to FIG. 6 but covering half the volume.

Other volume temporal measurement formats may be selected. With reference to FIG. 8, the control means 90 can again rotate 92 the gantry at 1 second/revolution. In this embodiment however, the patient is moved 94' axially only 7.5 cm/scan and the table retraces 98' the 7.5 cm in about 1.5 seconds. Again, the couch velocity 96' is substantially constant over the 5 second helical scanning time. In this embodiment, a volume half as large as in the embodiment of FIG. 6 but is scanned every 6.5 seconds, enabling 8 full scans per minute to be achieved.

Figure 9:
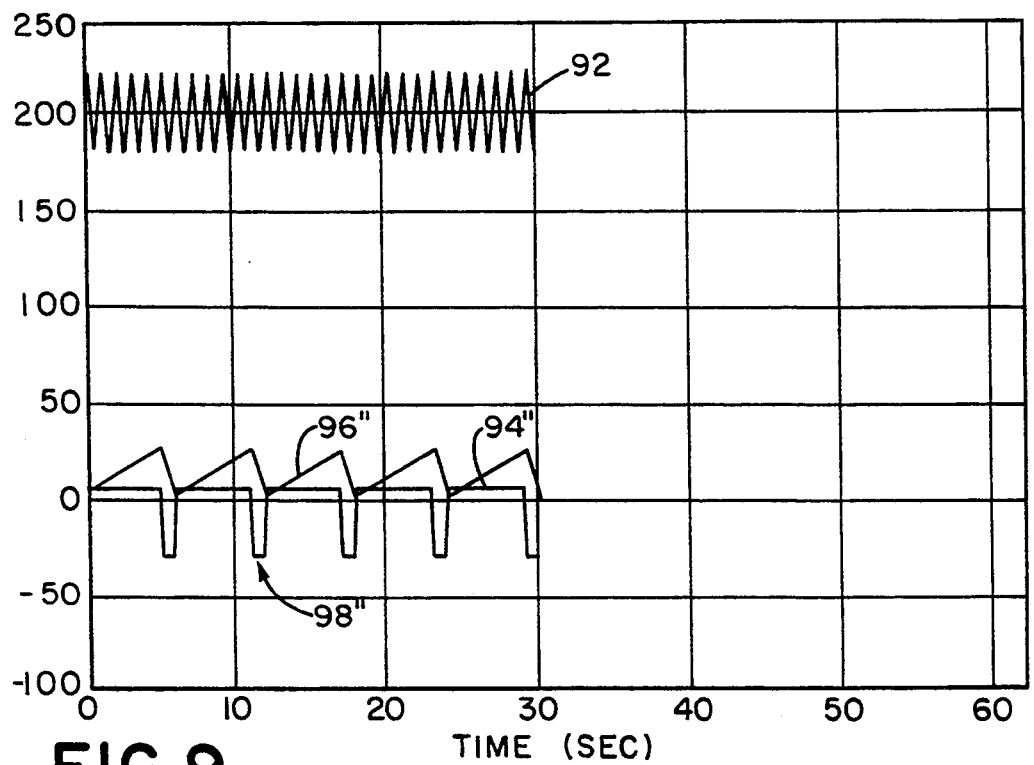
FIG. 9 is analogous to FIG. 6 for a 2.5 cm volume using a high resolution target scan.

With reference to FIG. 9, the gantry again rotates 92 at about 1 second/revolution. However, for higher resolution, the table moves 94" only 2.5 cm in the period of about 5 seconds. This enables the table to be stopped and returned 98" to the original position in about a second for about a 6 second scan. Thus, in this embodiment, 10 helical scans per minute can be achieved.

Figure 10:
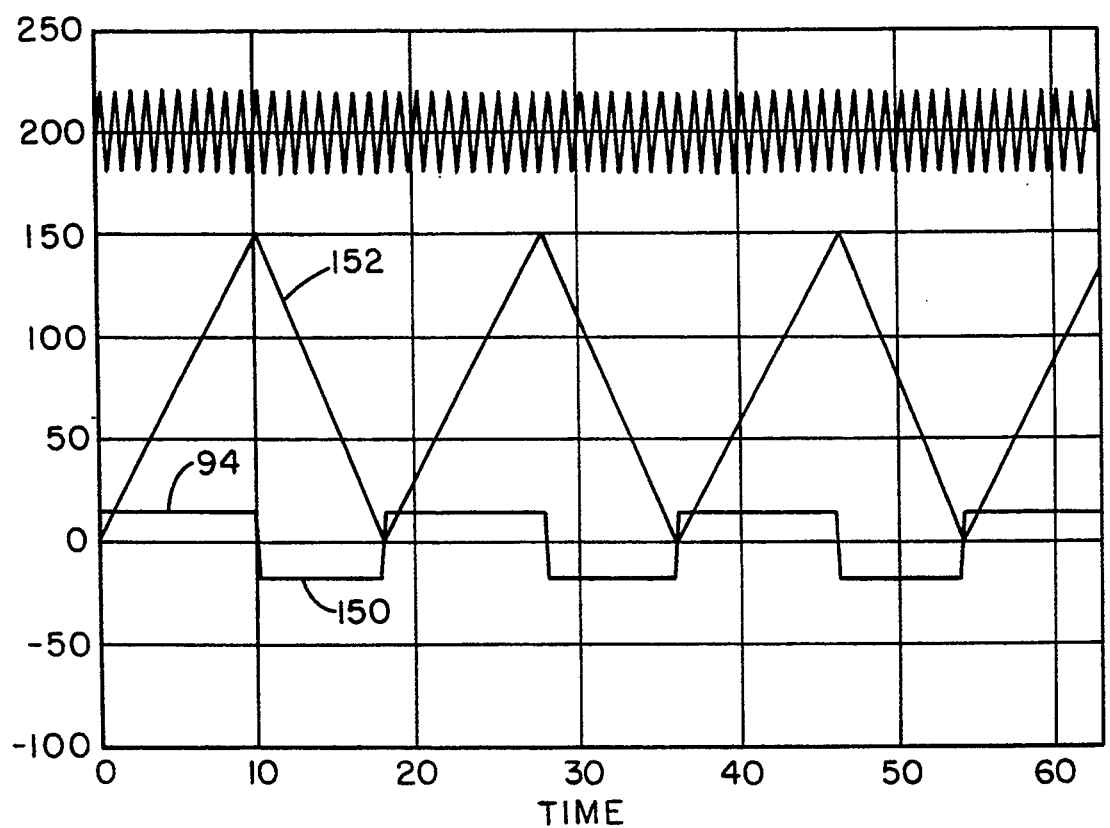
FIG. 10 is analogous to FIG. 6 but provides time for breathing between scans.

With reference to FIG. 10, the patient table scans 15 cm in about 10 seconds 94 while the patient holds his breath. A period 150 of about 8 seconds is provided for the patient to exhale and inhale again in preparation for the next breath-hold. During which breathing time the table is returned 152 to its initial starting position. In this manner, a scan can be achieved about every 18 seconds or about 4 scans in 64 seconds.

A human patient commonly has an oval cross section which changes the dynamic range of transmitted radiation with angular orientation. The synchronization control means 90 further controls a power supply 160 for the x-ray tube 20. The power supply adjusts the x-ray tube current or voltage generally in proportion to the mean attenuation path through the patient for each angular position of the x-ray tube. By varying the exposure in this manner, the quantum noise statistics of the reconstructed volume can be made more uniform.

When the gantry rotation or table speed are varied disproportionately, the scan becomes non-helical. However, (as demonstrated above), a suitable reconstruction volume can still be attained. For higher attenuation projections, either the gantry rotation or the table movement is slowed to compensate for the higher quantum noise. Analogously, if the x-ray tube voltage, the filtration, or the x-ray tube current is varied, a helical scan can still be performed. Specifically, the voltage filtration and/or current are increased for higher attenuative projections. The synchronization of these parameters may be either predetermined based on previous estimates or may be determined by estimates from earlier projections or scans of the same volume.

As discussed above, the views may be grouped into a group spanning 360° for 180° based reconstructions. The energy level (kV) of the x-ray tube in another embodiment is varied or alternated between two levels. By continuously varying the kV with a prescribed high to low variation as shown in 162 of FIG. 11A, two weighting functions (64, 166) can be applied to the respective projections to produce two sets of 180° based projections, both of which correspond to the same imaging plane. The average kV value for each ray in each set corresponds to either the high kV level or low kV level. Exactly 1½ rotations are required for each cycle from high kV to low kV back to high kV. The x-ray current 168 is varied counter cyclically to maintain the noise in both the high and low kV projections while minimizing the total exposure. Curve 164 identifies the high kV weighting function, $W_{hi}(R.180,\beta) = W_{hi}(\gamma,\beta)$.

With reference to FIG. 11B, the weighting function applied by the interpolating means 46 shifts for the high and low kV portions. That is, the weighting function curve 164 illustrates the preferred weighting function for the high kV or voltage projection rays whereas the weighting function curve 166 illustrates the weighting function used with the low energy rays. These ray projections are recombined into two separate 180° based sets or groups of projections. In the illustrated embodiment, the beam width corresponds to about three rings of the helix and a reconstructed image or slice is obtained for every one and a half rings of the helix.

With reference to FIG. 11C, the variation in weighting values for the extremes of the fan ($\beta = \pm\beta_o$) is illustrated for the high kV 180° based projection set. More specifically, weighting function curve 164 is shifted or swayed between curve 164a at one extreme ray of the fan and 164b at the other extreme ray of the fan. Analogous shifts are made for the weighting function 166 for the low kV projection set.

To increase the x-ray collection efficiency, a plurality of detectors are positioned adjacent to each other in the longitudinal direction. Positioning two detectors longitudinally enables the width of the radiation seen by each detector to be selectively adjusted at the detector. Analogously, three or more detectors can be disposed in longitudinal alignment. This enables data along three interleaved spirals to be collected concurrently. In one embodiment, the three spirals of data cover the same volume with a greater sampling density. This is particularly advantageous in the dual energy modes described above. Alternately, the speed of the patient table is tripled such that the three sets of detector collect data with the same sampling density but three times as fast.

Figure 12:
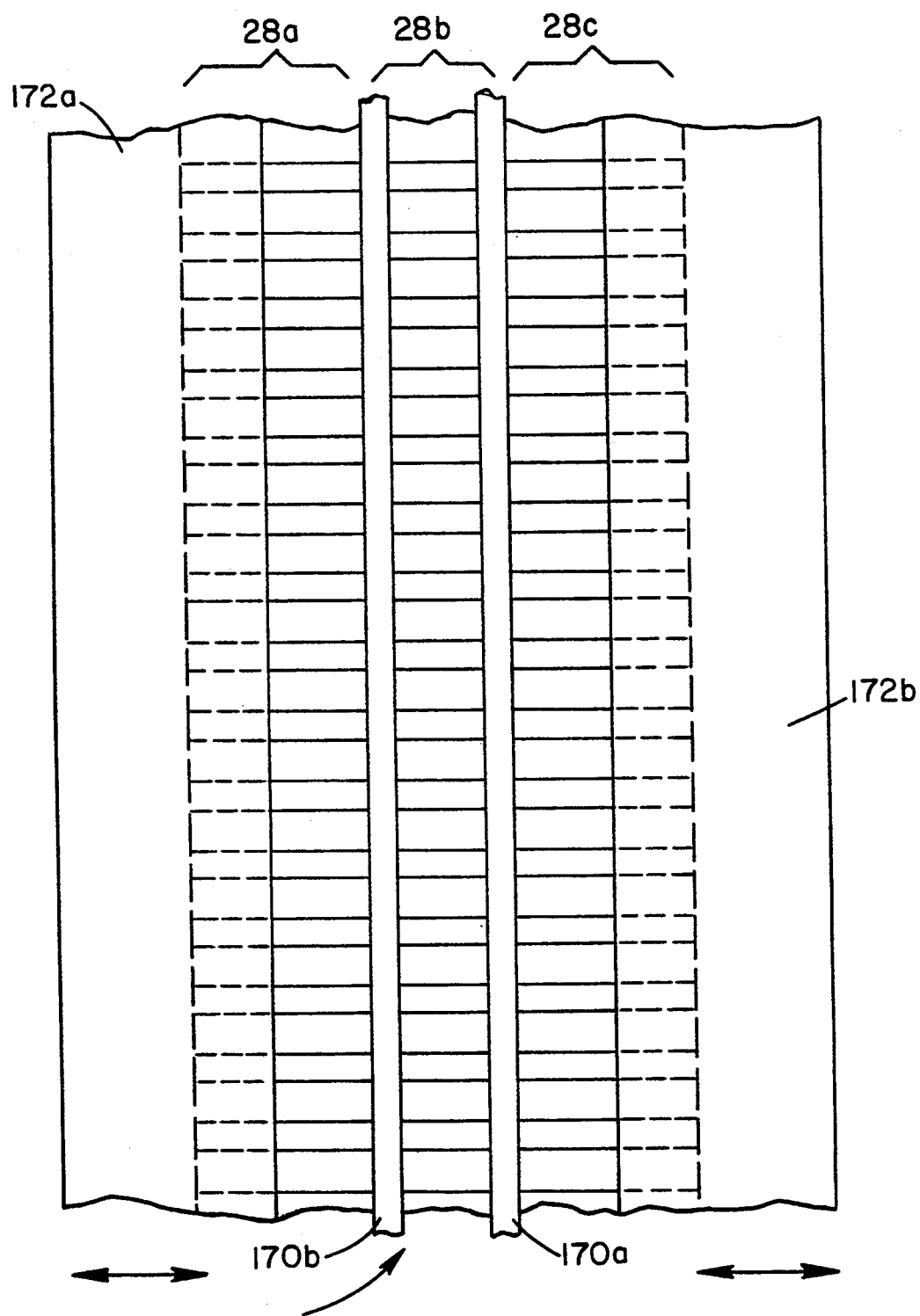
FIG. 12 illustrates a segmented detector array which enables multiple fan beams of data to be collected concurrently.

With reference to FIG. 12, the detector array 24 preferably includes a plurality of rings of detectors 28a, 28b, 28c. Collimators 170a, 170b selectively adjust the width of the beam striking the central detector ring 28b. Outer collimators 172a, 172b adjust the widths of the x-ray beams striking the outer detector rings 28a, 28c. In this manner, three x-ray beams are generated to collect data corresponding to three helices concurrently. Alternatively, a multi-spot x-ray tube may be utilized to increase the thickness of the x-ray beam such that the plurality of beams are more parallel.

Figure 1C:
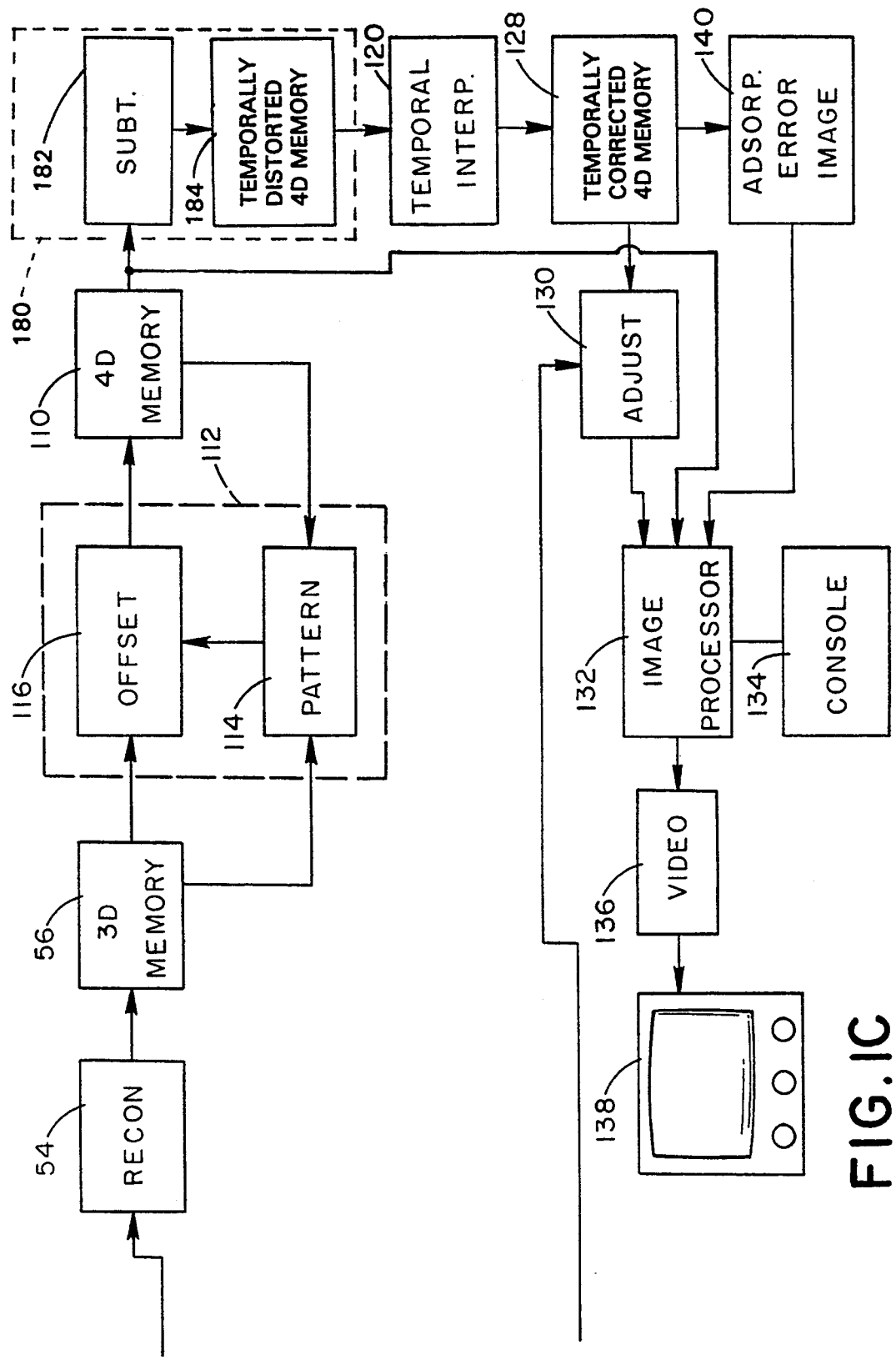
FIG. 1C is a diagrammatic illustration which is to be viewed in conjunction with FIG. 1A of an alternate embodiment to FIG. 1B.

With reference to FIG. 1C, it is to be appreciated that all of the reconstructed image data need not be temporally interpolated. Rather, the image data can be processed to derive medically significant image data parameters or information, such as average CT number within a specified region, absorption rates, blood flow maps, and the like.

More specifically, a processing means 180 processes the temporally distorted four-dimensional image representations in memory 10 to derive temporally distorted diagnostic parameters or information, e.g. average CT number within a specified region, average contrast values for specified parts of the human anatomy, or the like. In the illustrated embodiment, the processing means 180 includes a subtraction means 182 which subtracts a time equal to zero from one of the three-dimensional contrast image representations in the memory 110 which was generated from data collected prior to introduction of the contrast agent from subsequently collected three-dimensional contrast image representations taken at time intervals after introduction of the contrast agent. The series of differences taken together constitute a temporally distorted four-dimensional contrast image that is stored in a temporally distorted four-dimensional memory means 184. That is, the temporally distorted four-dimensional contrast image is a series of three-dimensional contrast agent concentration images with the data within each three-dimensional image taken over a significantly long period of time.

In regions of primary interest, the contrast agent concentration can be expected to increase with time. In peripheral regions which do not absorb the contrast agent, the contrast agent concentration remains zero. Thus, a large percentage of the four-dimensional image data is zeroed by the subtraction means simplifying and reducing the calculations required for temporal interpolation. The temporal interpolating means 120 temporally interpolates the temporally distorted four-dimensional contrast image from the temporally distorted four-dimensional memory to produce a four-dimensional temporally corrected contrast image for storage in the temporally corrected four-dimensional memory 128. The temporally corrected four-dimensional contrast image in memory 128 is subsequently processed as described above in conjunction with FIG. 1B.

Optionally, the time zero or reference image which represents the contrast agent free image may also be supplied to the image processor 132 to be converted into a display. For example, the contrast image can be presented as a color display with the reference image displayed more faintly in black and white to provide the radiologist with an image of the surrounding tissue to provide a frame of reference. It is to be appreciated that the processing means 180 can process the temporally distorted image in memory 110 to generate other time evolving diagnostic information for subsequent temporal interpolation.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of computed tomographic imaging comprising:
    (a) moving a radiation source and a subject relative to each other so as to irradiate a volume of a subject along a generally spiral path;
    (b) over time during the moving of the radiation source along the spiral path, collecting a spiral data set that includes a plurality of views of image data, each view being indicated by an angular position around the subject and by an angular position along a spiral, the views being progressively displaced in time;
    (c) reconstructing a three-dimensional reference image representation;
    (d) injecting the subject with a contrast agent;
    (e) repeating steps (a) and (b) over time to generate a plurality of temporally displaced spiral data sets, each data set having temporally displaced views;
    (f) temporally and spatially interpolating corresponding views of the spiral data sets and reconstructing the interpolated views into a plurality of temporally displaced three-dimensional image representations such that each three-dimensional image representation represents the volume at a common instant in time.

2. A method of computed tomographic imaging comprising:
    (a) moving a radiation source and a subject relative to each other so as to irradiate a subject along a generally spiral path;
    (b) progressively collecting a spiral data set that includes a plurality of progressively temporally displaced views of image data over a data collection duration, each view being indicated by an angular position around the subject and by an angular position along a spiral;
    (c) repeating steps (a) and (b) over time to generate a plurality of temporally displaced spiral data sets, each data set having progressively temporally displaced views;
    (d) spatially interpolating corresponding views within each spiral data set and reconstructing the spatially interpolated views into a plurality of temporally displaced three-dimensional image representations, each of the three-dimensional image representations being temporally distorted by being reconstructed from the temporally displaced views of image data collected over the collection duration;
    (e) temporally interpolating such that at least selected data in each of the temporally distorted three-dimensional image representations is corrected to correspond to a common time.

3. The method as set forth in claim 2 further including aligning each of the reconstructed three-dimensional image representations prior to the temporal interpolating step.

4. The method as set forth in claim 2 wherein in step (a), the radiation source rotates at a rate of about 1 revolution per second and the patient traverses axially for a preselected distance and further including:
    after the preselected distance, gating the radiation source off and returning the subject axially at a higher rate of speed to an initial starting position before repeating steps (a) and (b).

5. The method as set forth in claim 4 wherein the subject moves axially for not more than 10 seconds and the step of returning the subject to the initial starting position is achieved in not more than two seconds.

6. A method of contrast agent enhanced CT imaging comprising:
    (a) generating a three-dimensional reference image representation of a subject;
    (b) injecting the subject with a contrast agent;
    (c) after injecting the contrast agent, moving a radiation source and the subject relative to each other so as to irradiate the subject along a generally spiral path;
    (d) collecting a spiral data set that includes a plurality of views of image data, each view being indicated by an angular position around the subject and by an angular position along a spiral;
    (e) repeating steps (c) and (d) over time to generate a plurality of temporally displaced spiral data sets;
    (f) spatially interpolating corresponding views within each spiral data set and reconstructing the spatially interpolated views into a plurality of temporally displaced three-dimensional image representations illustrative of a time evolution of the contrast agent, whereby the plurality of three-dimensional image representations represent a common volume of the subject at time displaced intervals.

7. The method as set forth in claim 6 further including temporally interpolating such that inherently temporally distorted data in each of the three-dimensional image representations is corrected to remove the temporal distortion and correspond to a common time.

8. The method as set forth in claim 6 further including subtracting the three-dimensional reference image representation from each of the plurality of temporally displaced three-dimensional image representations to generate a series of temporally displaced volume image representations of the contrast agent.

9. The method as set forth in claim 8 further including selectively generating a two-dimensional human-readable display from the temporally displaced volume image representations of the contrast agent.

10. The method as set forth in claim 9 wherein the step of generating the human-readable display includes generating a display illustrating temporal progression of the contrast.

11. The method as set forth in claim 9 further including temporally interpolating the series of temporally displaced volume images such that each generated two-dimensional human-readable display corresponds to a common time.

12. The method as set forth in claim 9 further including:
- determining a contrast agent absorption rate for each voxel of the three-dimensional contrast image representations;
- comparing the contrast agent absorption rate with a preselected absorption curve; and,
- generating a human-readable image representation of the deviations between the determined contrast agent absorption rate and the preselected absorption curve.

13. A method of diagnostic imaging comprising:
(a) moving a subject and a radiation source such that a volume of interest of the subject is irradiated along a generally spiral path of a preselected axial length over a preselected duration;
(b) collecting a plurality of views of data each identifiable by a corresponding position along the spiral path and being temporally displaced over the preselected duration;
(c) spatially interpolating corresponding axially displaced views with a spatially interpolation function;
(d) reconstructing the spatially interpolated views into a three-dimensional image representation;
(e) repeating steps (a)-(d) a plurality of times to generate a plurality of the three-dimensional image representations which are linear in three spatial dimensions;
(f) temporally interpolating at least selected regions of the plurality of three-dimensional image representations to create a four-dimensional image representation in the three spatial dimensions and a time dimension, which four-dimensional image representation is linear in all four dimensions.

14. The method as set forth in claim 13 wherein a contrast agent is injected into the subject and subtracting a three dimensional image representation of the same volumetric region of the subject without contrast agent from the data from the four-dimensional image representation to generate a four-dimensional image representation representing movement of the contrast agent through the volume of interest with time.

15. A method of computed tomographic imaging comprising:
(a) moving a radiation source and a subject relative to each other so as to irradiate a subject along a generally spiral path;
(b) progressively collecting a spiral data set that includes a plurality of progressively temporally displaced views of image data over a data collection duration, each view being indicated by an angular position around the subject and by an angular position along a spiral;
(c) repeating steps (a) and (b) over time to generate a plurality of temporally displaced spiral data sets, each spiral data set having progressively temporally displaced views;
(d) spatially interpolating and reconstructing the views into a temporally displaced series of temporally distorted image representations, each of the temporally distorted image representations being temporally distorted by being reconstructed from the temporally displaced views of image data collected over the collection duration;
(e) processing the temporally distorted image representations to generate a temporally displaced series of temporally distorted diagnostic information representations;
(f) temporally interpolating the temporally distorted diagnostic information representations such that each is corrected to correspond to one of a series of common times.

16. The method as set forth in claim 15 wherein the temporally interpolated information representations include a temporally displaced series of three-dimensional contrast agent image representations.

17. In a computed tomographic imaging apparatus which includes a means for repeatedly moving a radiation source and a subject relative to each other such that the fan of radiation irradiates the subject along a generally spiral path over a data collection duration; radiation detectors for detecting the radiation fan and generating a plurality of temporally displaced views of electronic data, each view being identified by an angular position around the subject and by an angular position along a spiral; a spatial interpolating means for spatially interpolating corresponding views of each spiral; and a reconstructing means for reconstructing the temporally displaced, spatially interpolated views into a plurality of temporally distorted three-dimensional image representations, THE IMPROVEMENT COMPRISING:
- a temporal interpolating means for temporally interpolating the plurality of temporally distorted three-dimensional image representations such that the data in each of the three-dimensional image representations corresponds to a common time, whereby the three-dimensional image representations are corrected for temporal distortion caused by generating views over the data collection duration.

18. The apparatus as set forth in claim 17 further including an aligning means for aligning each of the three-dimensional image representations prior to the temporal interpolation.

19. The apparatus as set forth in claim 17 wherein the subject is injected with a contrast agent and further including a means for subtracting a reference image representation from each of the three-dimensional image representations to generate a series of temporally displaced image representations of the contrast agent.

20. The apparatus as set forth in claim 17 further including a video processor means for selectively generating a two-dimensional human-readable display from the temporally displaced three-dimensional contrast agent images.

21. A diagnostic imaging apparatus comprising:
- a means for repeatedly moving a subject and a radiation source such that the subject is irradiated along a generally spiral path over a preselected axial length over a preselected duration;
- a detector means for detecting radiation that has traversed the subject and producing a plurality of views of electronic data each identifiable by a corresponding position along the spiral path;
- a means for interpolating axially corresponding views with an interpolation function;
- a means for reconstructing the views into a plurality of temporally displaced, temporally distorted three-dimensional image representations; and, a temporal interpolation means for temporally interpolating the plurality of temporally distorted image representations to create a four-dimensional image representation in three physical dimensions and a time dimension, which four-dimensional image representation is linear in all four dimensions.

22. The apparatus as set forth in claim 21 wherein a contrast agent is injected into the subject and further including a means for subtracting a three dimensional image representation of the same volumetric region of the subject without contrast agent from the data of the four-dimensional image representation to generate a four-dimensional image representation representing movement of the contrast agent with time.

23. The apparatus as set forth in claim 22 further including a processing means for processing the temporally distorted image representations to derive temporally distorted processed parameter image representations which are temporally interpolated by the temporal interpreting means.

24. A diagnostic imaging apparatus comprising:
a means for repeatedly moving a radiation source and a subject relative to each other such that radiation from the source repeatedly traverses a common region of the subject along a plurality of spiral paths;
a detector means for detecting the radiation that has traversed the subject and producing a plurality of spiral data sets, each spiral data set including a plurality of progressively temporally displaced views of image data collected over one of the spiral paths during a spiral paths during a duration, each view being identified by a position along the spiral path;
a spatial interpolating means for spatially interpolating corresponding views within each spiral data set;
a reconstruction means for reconstructing the spatially interpolated views into a temporally displaced series of temporally distorted image representations, each of the temporally distorted image representations being temporally distorted by being reconstructed from the temporally displaced views of image data collected over the spiral path traversal duration;
a processing means for processing the temporally distorted image representations to generate a temporally displaced series of temporally distorted diagnostic information representations;
a temporal interpolating means for temporally interpolating the temporally distorted diagnostic information representations such that each is corrected to correspond to a one of a series of common times;
a display means for converting the temporally interpolated diagnostic information representations into a series of human-readable displays.

* * * * *